United States Patent
Toyoda et al.

(10) Patent No.: US 7,537,687 B2
(45) Date of Patent: May 26, 2009

(54) HEMODIALYSIS DEVICE

(75) Inventors: Masahiro Toyoda, Haibara-gun (JP); Yasushi Takakuwa, Haibara-gun (JP)

(73) Assignee: Nikkiso Co., Ltd., Tokyo (JP)

( * ) Notice: Subject to any disclaimer, the term of this patent is extended or adjusted under 35 U.S.C. 154(b) by 844 days.

(21) Appl. No.: 11/246,385

(22) Filed: Oct. 7, 2005

(65) Prior Publication Data
US 2006/0081517 A1     Apr. 20, 2006

(30) Foreign Application Priority Data
Oct. 15, 2004   (JP) .............................. 2004-301108

(51) Int. Cl.
*C02F 1/44*    (2006.01)
*A61M 1/16*    (2006.01)
(52) U.S. Cl. .................... 210/85; 210/321.6; 604/6.08; 604/6.09
(58) Field of Classification Search ................ 604/5.04, 604/6.09, 6.08, 6.11; 210/85, 645, 646, 647, 210/321.71, 321.6
See application file for complete search history.

(56) References Cited

U.S. PATENT DOCUMENTS 6,663,585 B1   12/2003   Ender
6,932,786 B2 *  8/2005   Giacomelli et al. ........ 604/6.08
2003/0036719 A1  2/2003   Giacomelli et al.

FOREIGN PATENT DOCUMENTS

JP    2003-518413 A    6/2003

* cited by examiner

Primary Examiner—Terry K Cecil
(74) Attorney, Agent, or Firm—Darby & Darby P.C.

(57) ABSTRACT

A hemodialysis device includes a hemodialysis device main body including an arterial blood circuit, venous blood circuit, blood pump, dialyzer, dialysate inlet and outlet lines, voltage adding device, electric potential measuring device, and monitoring device monitoring the needle when it is detached from the patient based on an electric potential measured by the electric potential measuring device. One electrode of the voltage adding device is attached between an arterial blood needle in the arterial blood circuit and the pump, and another electrode is attached to the dialysate outlet line. The hemodialysis device allows the precise detection of a needle that is detached from a patient taking a blood hemodialysis treatment by monitoring a voltage difference at a predetermined position while providing voltage to the blood flowing in the blood circuit. The device also allows the suppression of an increase in production cost for a disposable blood circuit.

11 Claims, 3 Drawing Sheets

HEMODIALYSIS DEVICE

INCORPORATION BY REFERENCE

The present application claims priority under 35 U.S.C. §119 to Japanese Patent Application No. 2004-301108 filed on Oct. 15, 2004. The content of the application is incorporated herein by reference in its entirety.

FIELD OF THE INVENTION

The present invention relates to a hemodialysis device which purifies blood from a patient in extracorporeal blood circulation.

BACKGROUND OF THE INVENTION

In general purification treatment such as hemodialysis treatment, a blood circuit including flexible tubing is used to place patient's blood in extracorporeal circulation. This blood circuit arrangement mainly includes an arterial blood circuit having an arterial needle at one end to collect blood from the patient and a venous blood circuit having a venous needle at one end to return the blood to the patient. A dialyzer between the arterial blood circuit and the venous blood circuit purifies the blood circulating extracorporeally.

Such a dialyzer is composed of plural hollow fibers inside the dialyzer. Blood flow inside each hollow fiber and the flow of dialysate outside the hollow fibers (i.e. between an external surface of the hollow fiber and an inside surface of a dialyzer case). The hollow fiber has a blood purification membrane with small pores on its surface. Wastes in the blood flowing inside the hollow fiber is discharged into the dialysate after passing the blood purification membrane and the blood, without the wastes, is returned to the patient. Also, a ultrafiltration pump installed inside the dialyzer to remove water from the patient's blood allows the removal of water during dialysis.

When a needle is detached from a patient to whom the needle had been attached during a hemodialysis treatment due to any reason, and especially when the arterial blood needle is detached from the patient, air is indrawn from the arterial blood needle and an air-lock is generated in the dialyzer. Also, when the venous blood needle is detached from the venous blood circuit, the patient's blood introduced from the arterial blood needle is wasted without returning to the patient. According to such failure, the pressure (venous blood pressure) of patient's blood flowing in the venous blood circuit is monitored to detect if the needle has dropped out. Specifically, when the needle is detached from the patient, the needle is open to the air and the blood pressure flowing in the venous blood circuit decreases so that the dropping out of the needle from the patient can be detected by detecting the blood pressure.

Normally the blood pressure (venous blood pressure), which is measured by a pressure sensor, changes depending on a number of factors, e.g., clogging in the dialyzer or a change of the condition of patient's blood during the hemodialysis treatment, so that the venous blood pressure is changeable even under normal conditions. Therefore, it is a drawback that judgment about whether the change of the pressure is due to a change of patient's position, which is normal, or due to a detachment of the venous blood needle, which is abnormal, cannot be carried out correctly.

Based on such reasoning, for example, as disclosed in Japanese Patent Publication No. 2003-518413, a hemodialysis device has voltage adding means (the voltage generator in the patent) for adding a voltage to the blood flowing in the blood circuit by adding a voltage between two electrodes, measuring means (the detector in the patent) for measuring a voltage difference at two positions according to the voltage added by the voltage adding means, and monitoring means (the calculation means in the patent) for obtaining the voltage difference by comparing the values measured by two measuring means. Specifically, as the measuring means is attached, the voltage difference obtained by the monitoring means varies when the needle is detached from the patient, and the detachment of the needle can be monitored effectively based on such change.

SUMMARY OF THE INVENTION

However, as both electrodes are attached to the blood circuit in the above traditional hemodialysis device, the following problems remain. Specifically, since the blood circuit should be disposed of after every hemodialysis treatment, as a so-called disposable part, and since the blood circuit has two electrodes attached, the blood circuit with two electrodes should be disposed of when the treatment is over. Accordingly, it is problematic because of high production cost. Further, as the wiring of the extracorporeal blood circuit in the traditional dialyzer is rather complex, medical staff who sets the device has to do more work or may make some wiring mistakes.

The present invention provides a hemodialysis device in which a detachment of the needle from the patient who is taking a hemodialysis treatment can be accurately monitored by monitoring the voltage difference at a predetermined position while a voltage is added to the blood flowing in the blood circuit. Also, the increase of the production cost of the blood circuit which is disposable can be suppressed.

The present invention provides a hemodialysis device including a blood circuit having an arterial blood circuit and a venous blood circuit which circulates extracorporeally the blood collected from the patient, a blood pump disposed in the arterial blood circuit, a blood purification device that is connected between the arterial blood circuit and the venous blood circuit and that purifies the blood flowing in the blood circuit, a main body having a dialysate inlet line and a dialysate outlet line having an inlet and outlet, respectively, dialysate to and from the blood purification device, a voltage adding means having two electrodes that apply voltage to the blood flowing in the blood circuit between these electrodes, a measuring means detecting electric potentials where at least two positions where the voltage is added by the voltage adding means, and a monitoring means calculating the electric potential by comparing each electric potential detected by the measuring means and monitoring a detachment of the arterial blood needle or of the venous blood needle from the patient. One electrode of the voltage adding means is disposed between the arterial blood needle in the arterial blood circuit, and the blood pump and the other electrode is disposed in the dialysate inlet line or in the dialysate outlet line.

The present invention also provides a hemodialysis device in which at least one of the measuring means measures an electric potential of one of the electrodes in the voltage adding means.

Further, the present invention provides the hemodialysis device in which the voltage adding means or the measuring means directly contacts the blood or the dialysate to add the voltage or to detect the electric potential.

The present invention also provides the hemodialysis device in which the monitoring means calculates the electric potential by extracting a frequency component of the measured value measured by the measuring means.

According to an embodiment of the present invention, as the other electrode is disposed in the dialysate inlet line or the dialysate outlet line of the main body of the hemodialysis device, a detachment of the needle from the patient who is taking a hemodialysis treatment is monitored by monitoring the electric potential of a predetermined position while a voltage is added to the blood flowing in the blood circuit. Also, an increase of the production cost of the blood circuit which is disposable can be suppressed.

Further, according to an embodiment of the present invention, as at least one of the measuring means measures the electric potential of one of the electrodes in the voltage adding means, a connection part of the measuring means and one of the electrodes of the voltage adding means can be incorporated into the same part to further suppress an increase in the production cost.

According to an embodiment of the present invention, since the voltage adding means or the measuring means directly contacts the blood or the dialysate and adds a voltage or measures an electric potential, the measuring means can detect accurately the electric potential even if the voltage added by the voltage adding means is very low. Also, the monitoring means can monitor securely the detachment of the needle.

Further, according to an embodiment of the present invention, as the monitoring means measures the electric potential by extracting a frequency component of the measured value measured by the measuring means, the voltage added by the voltage adding means can be decreased and an accuracy of detection by the measuring means can be increased.

BRIEF DESCRIPTION OF DRAWINGS

The foregoing and other features of the present invention will be more readily apparent from the following detailed description and drawings of the illustrative embodiments of the invention wherein like reference numbers refer to similar elements and in which.

DETAIL DESCRIPTION OF THE EMBODIMENTS

Figure 1:
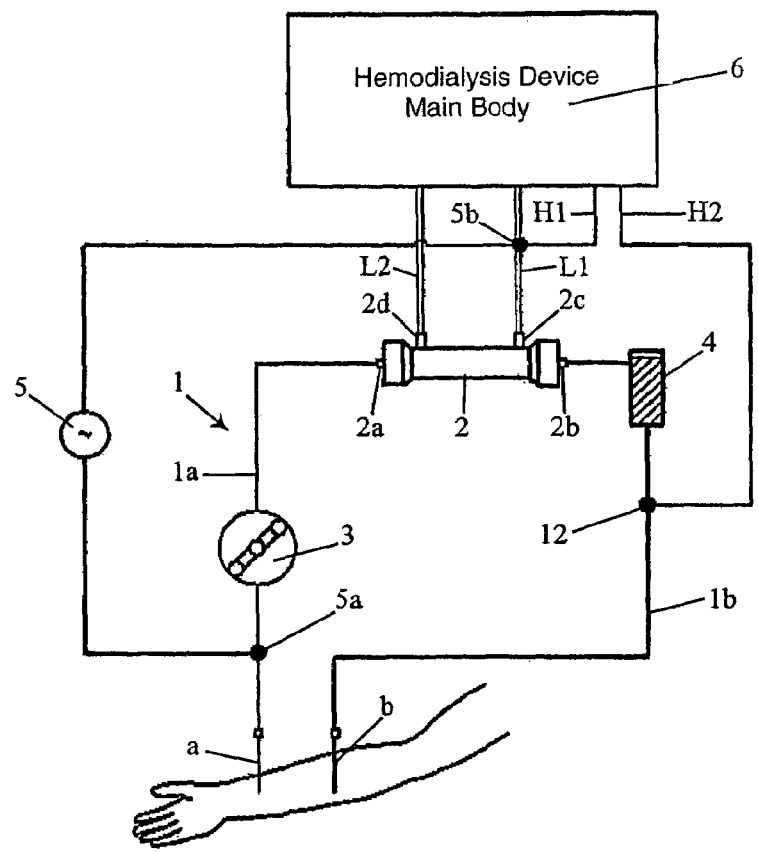
FIG. 1 is a schematic diagram of the hemodialysis device of an embodiment of the present invention.

The embodiments of the present invention are explained using figures. The hemodialysis device according to the present embodiments is a device to purify the patient's blood by extracorporeal circulation and is applied to a dialyzer which is used for hemodialysis treatment. The dialyzer includes, as shown in FIG. 1, blood circuit attached dialyzer 2, which is a blood purification device, and hemodialysis device main body 6 for supplying dialysate to dialyzer 2 and removing water. Blood circuit 1 includes mainly, as shown the same figure, arterial blood circuit 1a and venous blood circuit 1b, which are made from flexible tubing. Dialyzer 2 is installed between arterial blood circuit 1a and venous blood circuit 1b.

Arterial needle a is attached to the end of arterial blood circuit 1a and peristaltic blood pump 3, and venous needle b is attached to the end of venous blood circuit 1b, and drip chamber 4 for removing bubbles is attached in the middle of venous blood circuit 1b.

When peristaltic blood pump 3 is driven while arterial needle a and venous needle b are provided to the patient, the blood of the patient flows through arterial blood circuit 1a and into dialyzer 2 which purifies the blood. The purified blood returns to the patient through venous blood circuit 1b after air bubbles are removed in drip chamber 4. Thus, the blood of the patient is purified by dialyzer 2 while extracorporeally circulating through blood circuit 1.

Several ports are located on a case that houses dialyzer 2, such as blood inlet port 2a, blood outlet port 2b, dialysate inlet port 2c, and dialysate outlet port 2d. Blood inlet port 2a and blood outlet port 2b are connected to the end of arterial blood circuit 1a and venous blood circuit 1b, respectively. Dialysate inlet port 2c and dialysate outlet port 2d are connected to dialysate inlet line L1 and dialysate outlet line L2, respectively. Dialysate inlet and outlet lines L1 and L2 extend from hemodialysis device main body 6.

The dialyzer 2 includes multiple hollow fibers. The blood flows inside the hollow fibers, and the dialysate flows between the outside surface of the hollow fibers and the inside surface of the dialyzer case. The hollow fibers include many micropores that are located in the outside and the inside surface of the hollow fiber membrane, and through which waste products in the blood are dialyzed to the dialysate.

Further, one electrode 5a is attached between arterial needle a and peristaltic blood pump 3 in arterial blood circuit 1a, another electrode 5b is attached to dialysate inlet line L1, and voltage adding means 5 (voltage adding device) adding a voltage to the blood flowing in blood circuit 1 is connected to these electrodes 5a, 5b. When a voltage is added by voltage adding means 5, the blood is partially blocked and is under a non-conductive condition by squeezing action of peristaltic blood pump 3 at the position where peristaltic blood pump 3 is disposed. Accordingly, an electric current flows in the blood and the dialysate in the circuit between one electrode 5a including arterial needle a, venous needle b, and the other electrode 5b.

Specifically, when a voltage is added by voltage adding means 5 during a hemodialysis treatment, the electric current flows in blood and dialysate flowing in arterial blood circuit 1a, arterial needle a, inside body of the patient, venous needle b, venous blood circuit 1b, the blood pathway in dialyzer 2 and the pathway of the dialysate, and dialysate inlet line L1 as a closed circuit. Further, measuring means 12 (measuring device) for measuring an electric potential of the blood flowing in the lower stream side of drip chamber 4 in venous blood circuit 1b is installed in the same lower stream side (venous needle b side). Further, the blood and the dialysate are under a conductive condition through the membrane of dialyzer 2.

Figure 2:
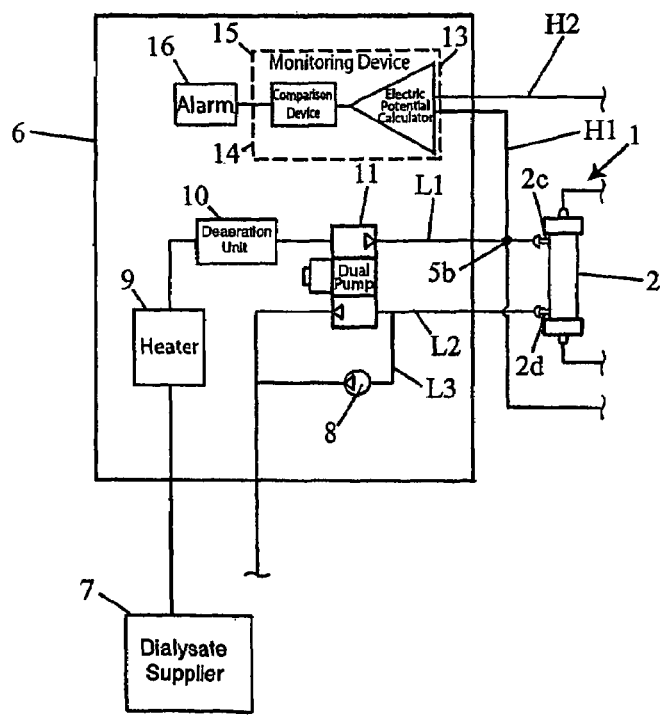
FIG. 2 is a schematic diagram of the hemodialysis device main body which is applied to the hemodialysis device of the present invention.

Further, as shown in FIG. 2, hemodialysis device main body 6 includes duplex pump 11 connected between dialysate inlet line L1 and dialysate outlet line L2, bypass line L3 connected to dialysate inlet line L2 bypassing duplex pump 11, and ultrafiltration pump 8 connected to bypass line L3. Additionally, one end of dialysate inlet line L1 is connected to dialyzer 2 (dialysate inlet port 2c) and the other end is connected to dialysate supplier 7 which prepares the dialysate of predetermined concentration.

One end of dialysate outlet line L2 is connected to dialyzer 2 (at dialysate outlet port 2d). The other end of dialysate outlet line L2 is connected to water fluid disposal means (not shown). The dialysate supplied from dialysate supplier 7 passes through dialysate inlet line L1 to dialyzer 2, dialysate outlet line L2 and bypass line L3, and is let out to the water fluid disposal means. In FIG. 2, a heater 9 and a deaeration unit 10 are both connected to dialysate inlet line L1.

Ultrafiltration pump 8 for concentrating the blood removes water from the blood of the patient flowing through dialyzer 2. When ultrafiltration pump 8 is activated, the volume of dialysate let out of dialysate outlet line L2 is greater than that of dialysate introduced from dialysate inlet line L1 because duplex pump 11 is quantitative; and water is removed from the blood by the difference of the inlet and outlet volume. Alternatively, instead of ultrafiltration pump 8, other means (e.g. utilizing a balancing chamber) can be used to remove water from the blood of the patient.

Monitoring means 15 (monitoring device) including electric potential calculator 13 and comparison device 14 is disposed in hemodialysis device main body 6. Electric potential calculator 13 is connected to other electrode 5b and measuring device 12 through wiring H1 and H2. Thus, the electric potential (known in the present embodiment) at other electrode 5b is measured, which is sent to electric potential calculator 13. Specifically, as other electrode 5b functions as both voltage adding device 5 and the connection point of measuring device 12, it can suppress an increase in production cost for blood circuit 1 in comparison with another device having two measuring device without sharing functions.

Further, voltage adding device 5 of the present embodiment is composed of an alternator so that the measured values of other electrode 5b and measuring device 12 are changed to direct-current by a smoothing circuit at electric potential calculator 13 to obtain the electric potential between both positions. Then, the difference in electric potential is sent to comparison device 14. Comparison device 14 monitors whether the electric potential measured is changed or not by comparing it with the base value (the difference of electric potential when arterial needle a and venous needle b are normally attached and normal treatment is being carried out). If the measured electric potential is changed, comparison device 14 decides that a needle dropped from the patient and activates an alarm 16.

Specifically, when arterial needle a and venous needle b are normally attached to the patient, as described, an electric current flows in the closed circuit including both needles a and b and approximately the same electric potential as the base value. When a needle is dropped from the patient, the circuit is blocked so that no electric current flows and the electric potential measured decreases closely to zero. Monitoring device 15 monitors such change of the electric potential so that a detachment of arterial needle a or venous needle b from the patient can be detected.

When monitoring device 15 determines that a detachment of arterial needle a or venous needle b from the patient is detected, alarm 16 sends a notice to medical staff by device of, e.g., a predetermined sound from a speaker, turning on or flashing an alarm light, or using a display (not shown). Further, when the electric potential is changed largely from the base value by monitoring device 15, in addition to or instead of alarm 16, peristaltic blood pump 3 can be stopped, e.g., as an interruption of the hemodialysis treatment.

Further, the connection point of one electrode 5a and other electrode 5b of voltage adding device 5 and measuring device 12, which directly contacts the blood flowing in arterial blood circuit 1a or the dialysate flowing in dialysate inlet line L1, adds a voltage or measures an electric potential. For example, it is preferable that a T-tube to which the electrode and the connection point are inserted is connected at the position where these electrode and connection point contacting the blood pathway or the dialysate pathway are disposed. Accordingly, as measuring device 12 and other electrode 5b can measure an electric potential even if the voltage added by voltage adding device 5 is very small, detachment of needle a or b can be surely monitored with monitoring device 15.

According to the above embodiment, not only an electric potential at a predetermined position is monitored while adding a voltage to the blood and the dialysate during a hemodialysis treatment, but also other electrode 5b is disposed in dialysate inlet line L1 of the hemodialysis device main body. Therefore, an increase in the production cost of blood circuit 1 which is a disposable part can be suppressed.

Figure 3:
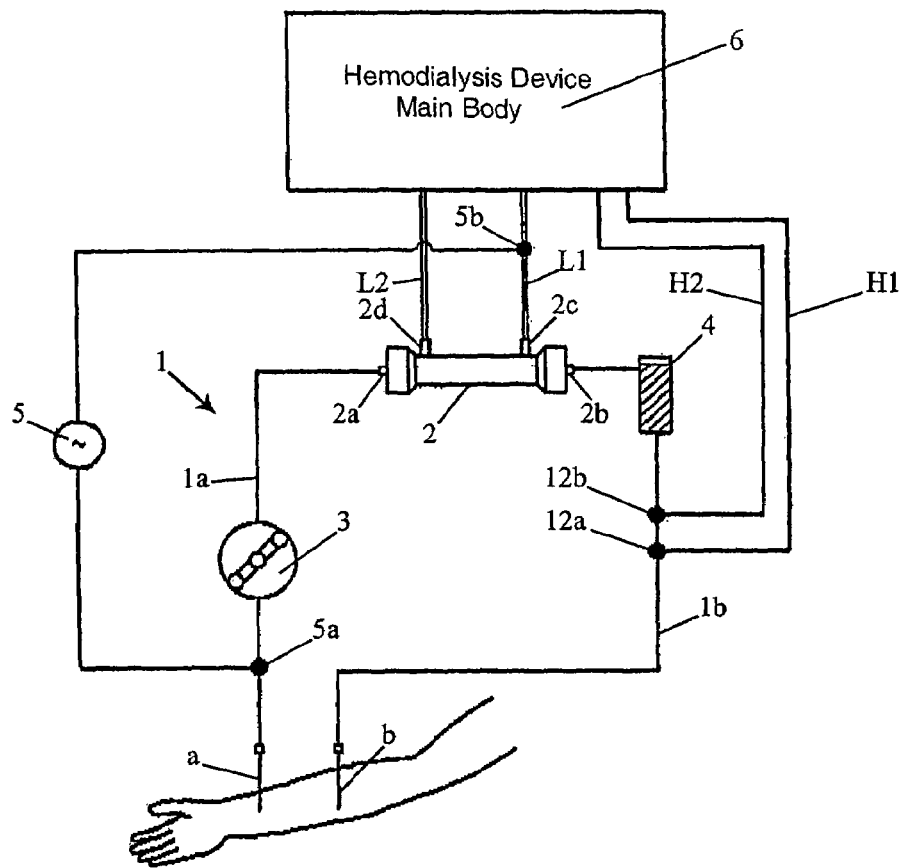
FIG. 3 is a schematic diagram of the hemodialysis device of another embodiment of the present invention.
Figure 4:
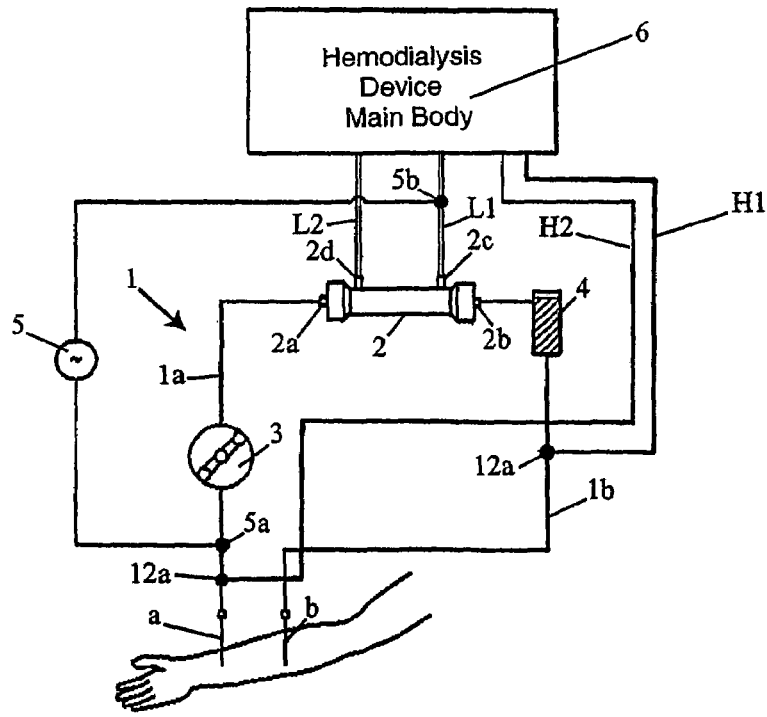
FIG. 4 is a schematic diagram of the hemodialysis device of another embodiment of the present invention.
Figure 5:
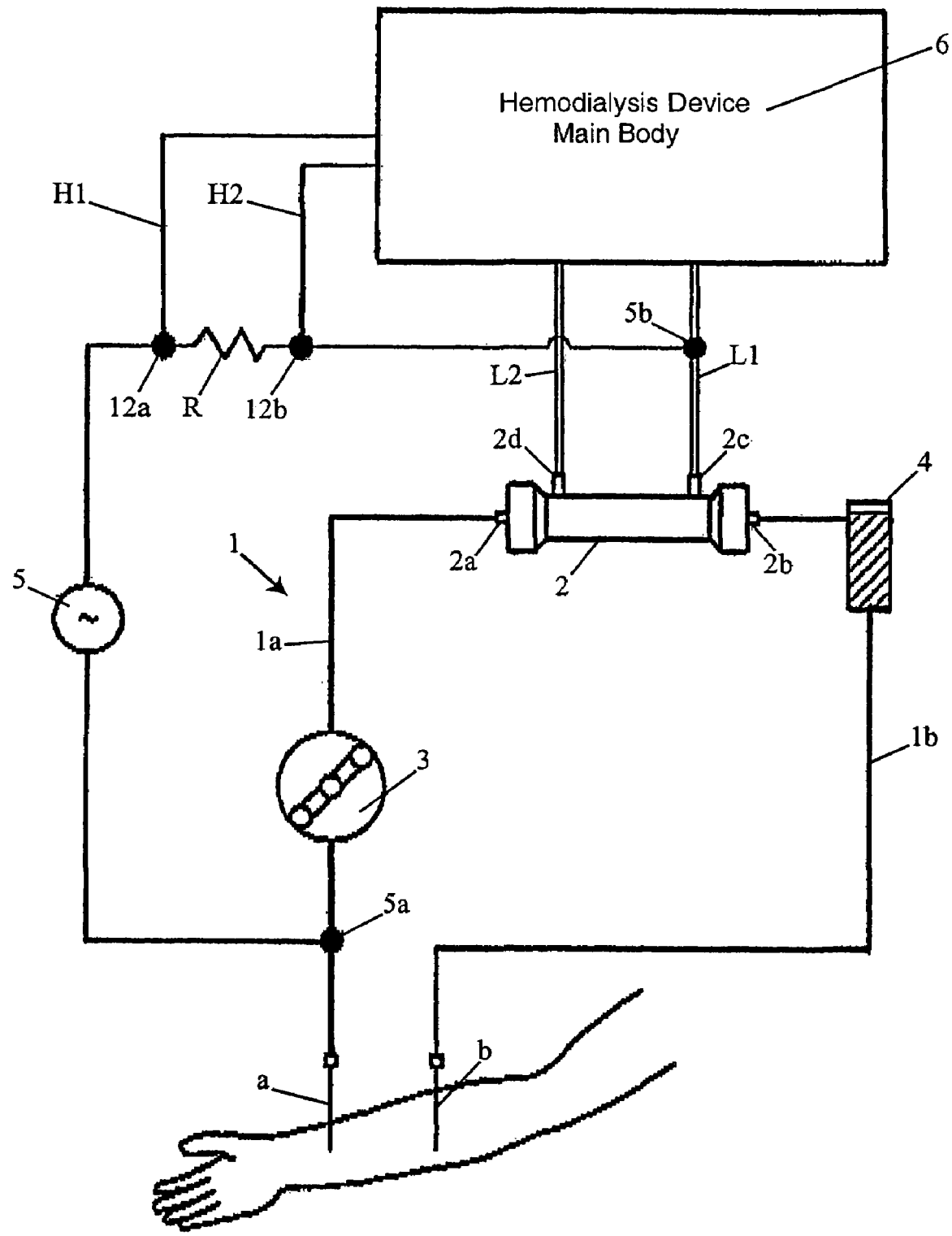
FIG. 5 is a schematic diagram of the hemodialysis device of another embodiment of the present invention.

The present invention is not limited to the above embodiment. For example, the embodiments shown in FIGS. 3 to 5 are acceptable. Specifically, referring to FIG. 3, one electrode 5a is disposed between arterial needle a and peristaltic blood pump 3 in arterial blood circuit 1a and other electrode 5b is disposed in dialysate inlet line L1. Measuring device 12a, 12b for measuring an electric potential accompanying the voltage added by voltage adding device 5 are disposed in the lower stream side (venous needle b side) of drip chamber 4 in venous blood circuit 1b. Referring to FIG. 4, one electrode 5a, other electrode 5b and measuring device 12a are disposed as in FIG. 3, and measuring device 12b is disposed in the upper stream side (arterial needle a side) of other electrode 5a in arterial blood circuit 1a.

According to these other embodiments, an electric potential measured by measuring device 12a, 12b changes in comparison with a base value (the electric potential referring to FIG. 3 decreases and the electric potential referring to FIG. 4 increases) when arterial needle a or venous needle b drops from the patient during a hemodialysis treatment. As a result, not only a detachment of needle a, b can be securely detected by monitoring a difference in voltage at a predetermined position while adding voltage to the blood and the dialysate under a hemodialysis treatment, but also an increase in the production cost of blood circuit 1 which is a disposable part can be suppressed because other electrode 5b is disposed in dialysate inlet line L1 of hemodialysis device main body 6.

Further referring to FIG. 5, two measuring device 12a, 12b are disposed on the wiring extending to other electrode 5b from voltage adding device 5, and also the wiring has resistance R having the equivalent impedance to the blood flowing in blood circuit 1. Even using such a hemodialysis device, not only a detachment of a needle from the patient can be monitored based on the difference of voltage measured by measuring device 12a, 12b, but also an increase of the production cost of blood circuit 1 which is a disposable part can be suppressed because measuring device 12a, 12b besides other electrode 5b of voltage adding device 5 are not disposed in blood circuit 1.

Further according to the present embodiment, instead of changing the measured value measured by the measuring means to direct-current in electric potential calculator 13, a composition which monitors the change of difference of electric potential by monitoring strength of a frequency component extracted by, e.g., frequency analysis and band pass filter, can be employed. According to such a composition, the voltage added by voltage adding device 5 can be decreased and accuracy of measurement can be increased.

Further, instead of using alternate current in the voltage adding device, means for providing direct-current can be used. An electrode of the voltage adding device and a connection point of the measuring device can be a capacity coupling type (which indirectly adds a voltage by disposing electric conductive material surrounding the blood circuit) instead of the above liquid contacting type (which directly contacts the blood or the dialysate). Thus, addition of a voltage by the voltage adding device as above can be carried out continuously during the hemodialysis treatment or can be carried out intermittently. If it is carried out intermittently, the effect of suppressing anxiety of the patient due to addition of a voltage can be expected.

Further according to the present embodiment, other electrode 5b can be disposed in dialysate inlet line L1, but instead of L1, it can be disposed in line 2. Referring to FIG. 1, one electrode 5a and the measuring device 12 can be the same electrode, but also the other electrode 5b and the measuring device 12 can also be the same electrode. Thus, in an embodiment, electrode 5a can act as both an electrode or the emission side of voltage adding device 5 and act as measuring device, taking a potentiometric reading. Also, electrode 5b can act as a ground for the voltage adding device 5 and as a measuring device 12. Further according to the present embodiment, hemodialysis device main body 6 does not house a mechanism for supplying dialysate, but it can be included in a personal-type dialyzing device which houses a mechanism for supplying dialysate.

If a hemodialysis device in which one electrode of a voltage adding device is disposed between an arterial needle and a blood pump in the arterial blood circuit and also if the other electrode is disposed in the dialysate inlet line or in the dialysate outlet line, the present invention also can be applied to such a device not withstanding having a different outer appearance or function.

We claim:

1. A hemodialysis device for purifying blood collected from a patient comprising;
    a blood circuit comprising an arterial blood circuit and a venous blood circuit which circulates the blood extracorporeally;
    a blood pump disposed in the arterial blood circuit;
    a blood purification device that is connected between the arterial blood circuit and the venous blood circuit and purifies the blood flowing in the blood circuit;
    a main body having a dialysate inlet line and a dialysate outlet line which inlet and outlet dialysate to and from the blood purification device, respectively;
    a voltage adding device comprising one electrode and another electrode adding voltage to the blood flowing in the blood circuit between the electrodes;
    a measuring device detecting electric potentials of at least two positions accompanying the voltage added by the voltage adding device; and
    a monitor calculating a calculated electric potential by comparing each electric potential detected by the measuring device and monitoring a detachment of an arterial blood needle or a venous blood needle from the patient;
    wherein one electrode of the voltage adding device is disposed between the arterial blood needle in the arterial blood circuit and the blood pump and the other electrode is disposed in the dialysate inlet line or the dialysate outlet line.

2. A hemodialysis device according to claim 1, wherein the measuring device measures an electric potential of the one electrode or the other electrode in said voltage adding device.

3. A hemodialysis device according to claim 2, wherein said voltage adding device or said measuring device directly contacts the blood or the dialysate to add the voltage or detect the electric potential.

4. A hemodialysis device according to claim 2, wherein said monitor calculates the calculated electric potential by extracting a frequency component of at least one of the electric potentials measured by the measuring device.

5. A hemodialysis device according to claim 1, wherein said voltage adding device or said measuring device directly contacts the blood or the dialysate to add the voltage or to detect the electric potential.

6. A hemodialysis device according to claim 5, wherein said monitor calculates the calculated electric potential by extracting a frequency component of at least one of the electric potentials measured by the measuring device.

7. A hemodialysis device according to claim 1, wherein said monitor calculates the calculated electric potential by extracting a frequency component of at least one of the electric potentials measured by the measuring device.

8. A hemodialysis device for purifying blood collected from a patient comprising;
    a blood circuit comprising an arterial blood circuit and a venous blood circuit which circulates the blood extracorporeally;
    a blood pump disposed in the arterial blood circuit;
    a blood purification device that is connected between the arterial blood circuit and the venous blood circuit and purifies the blood flowing in the blood circuit;
    a main body having a dialysate inlet line and a dialysate outlet line which inlet and outlet dialysate to and from the blood purification device, respectively;
    a voltage adding device comprising one electrode and another electrode adding voltage to the blood flowing in the blood circuit between the electrodes;
    a measuring device detecting electric potentials of at least two positions accompanying the voltage added by the voltage adding device; and
    a monitor calculating a calculated electric potential by comparing each electric potential detected by the measuring device and monitoring a detachment of an arterial blood needle or a venous blood needle from the patient;
    wherein one electrode of the voltage adding device is disposed between the arterial blood needle in the arterial blood circuit and the blood pump and the other electrode is disposed in the dialysate inlet line or the dialysate outlet line.

9. A hemodialysis device according to claim 8, wherein the measuring device measures an electric potential of the one electrode or the other electrode in said voltage adding device.

10. A hemodialysis device according to claim 8, wherein said voltage adding device or said measuring device directly contacts the blood or the dialysate to add the voltage or detect the electric potential.

11. A hemodialysis device according to claim 8, wherein said monitoring device calculates the calculated electric potential by extracting a frequency component of at least one of the electric potentials measured by the measuring device.

* * * * *